United States Patent [19]

Eriksen et al.

[11] Patent Number: 4,492,673
[45] Date of Patent: Jan. 8, 1985

[54] DISPOSABLE SOBRIETY TESTER

[75] Inventors: Wilbur R. Eriksen, Irvine; Harry E. Payne, Jr., Mission Viejo, both of Calif.

[73] Assignee: Sobryco, Inc., El Segundo, Calif.

[21] Appl. No.: 528,987

[22] Filed: Sep. 2, 1983

[51] Int. Cl.³ .......................... G01N 1/22; G01N 21/78
[52] U.S. Cl. .................................................... 422/85
[58] Field of Search .................. 128/719; 422/84–86, 422/88, 61, 55–59, 900; 436/132, 164, 169, 167

[56] References Cited

U.S. PATENT DOCUMENTS

| 3,437,449 | 4/1969 | Luckey | 436/167 X |
| 3,676,072 | 7/1972 | Krivis | 422/85 X |
| 3,734,692 | 5/1973 | Lucker et al. | 128/719 |
| 4,017,597 | 4/1977 | Reynolds | 422/159 X |
| 4,368,118 | 1/1983 | Siposs | 210/136 |

Primary Examiner—Barry S. Richman
Assistant Examiner—Michael S. Gzybowski
Attorney, Agent, or Firm—Harry G. Weissenberger

[57] ABSTRACT

A small, unitary, disposable sobriety self-tester of the balloon type in which a mouthpiece and a chemical indicator tube are permanently mounted on one side of an apertured base plate whose other side opens into a balloon sealed to the base plate. The mouthpiece and indicator tube may be sealed and filled with an inert gas so as to avoid the need for desiccants in the system, and thereby improve its ease of operation.

7 Claims, 4 Drawing Figures

DISPOSABLE SOBRIETY TESTER

This invention concerns sobriety testing devices, and more particularly, a simple, small, inexpensive, single-use device for allowing individuals to check their own alcohol levels prior to driving.

BACKGROUND

Sobriety tests are normally administered by law enforcement authorities after a person suspected of intoxication has been arrested, e.g. for drunk driving. The suspect usually has no way of knowing, prior to driving, whether he is sufficiently intoxicated to be committing an illegal act by getting behind the wheel.

The problem arises from the fact that existing sobriety test equipment is generally expensive enough to prevent its widespread availability to the general public, and awkward enough to use to prevent its routine use by intoxicated persons without assistance. Typically, existing equipment requires parts to be assembled, and desiccant to be removed, before each test is conducted. Consequently, a need exists for a small, inexpensive one-piece sobriety testing device which can be made widely available in bars and stores; is simple enough to give reasonably accurate readings in the hands of users who are unskilled and sufficiently intoxicated to be concerned about their lack of sobriety; and can be discarded after use.

SUMMARY OF THE INVENTION

The invention fills the above-discussed need for providing a small, unitary test device of the balloon type which can be sealed during manufacture after being filled with an inert gas, so that a user can obtain an accurate reading without assembling anything (and, in a preferred embodiment, without discarding any desiccant), merely by removing the seal, blowing into the mouthpiece, and observing the indicator after a predetermined length of time.

The device of this invention consists basically of a rigid mounting plate to which a mouthpiece, balloon and indicator are permanently attached in airtight relation. The mouthpiece is preferably provided with a check valve to prevent escape of air from the balloon except through the indicator. In a preferred embodiment of the invention, the mouthpiece and indicator are capped by separate, airtight seals. This allows the mouthpiece and indicator to be filled at the factory with an inert gas, thereby dispensing with the need for a desiccant which would have to be removed by the user prior to use.

It is thus the object of the invention to provide a small, disposable unitary sobriety testing device of the balloon type whose operation requires no manual dexterity or ability to follow more than rudimentary instructions.

It is another object of the invention to provide a field sobriety tester of the balloon type whose size, cost, construction and packaging allows it to be widely distributed to the general public.

BRIEF DESCRIPTION OF THE PREFERRED EMBODIMENT

Figure 1:
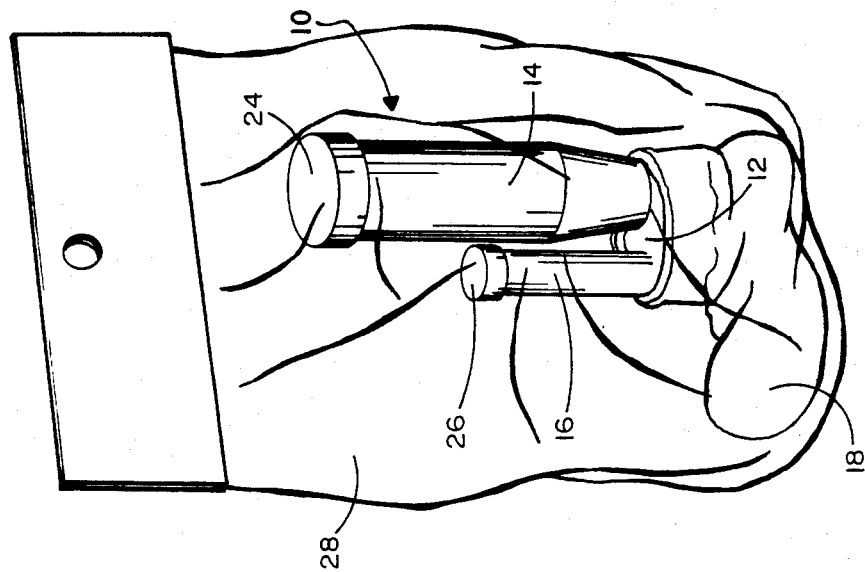
FIG. 1 is a perspective view showing the device of this invention in its packaged point-of-sale form.
Figure 2:
FIG. 2 is a perspective view showing the device's balloon being inflated prior to a measurement.
Figure 3:
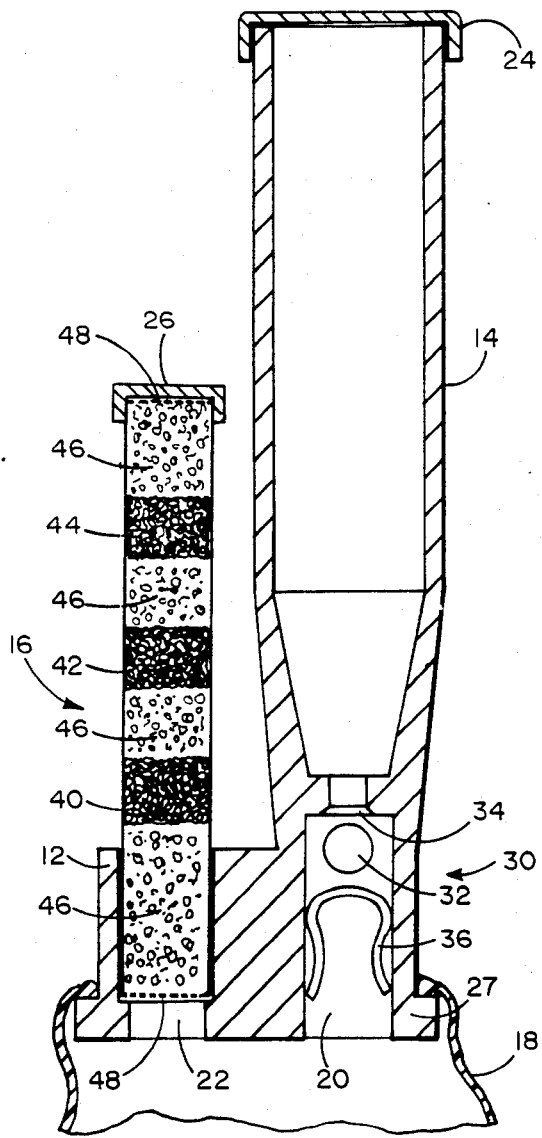
FIG. 3 is a vertical section of the device.
Figure 4:
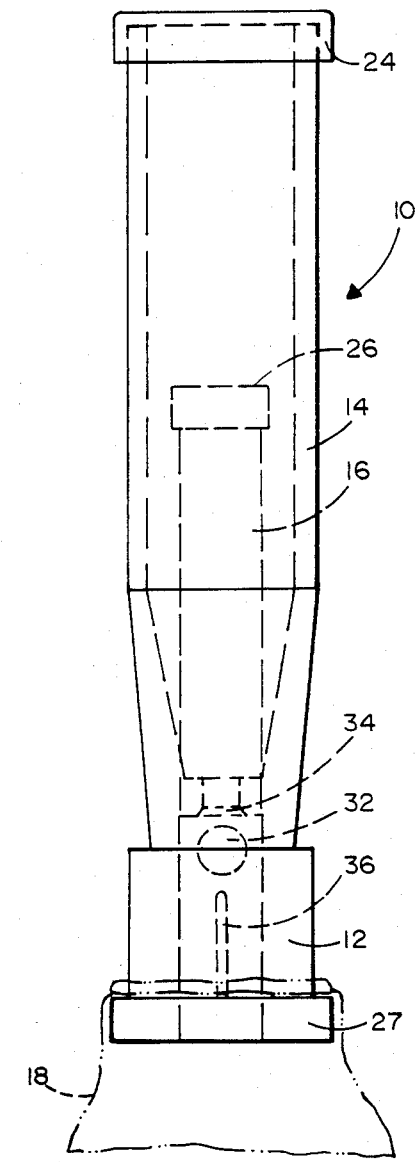
FIG. 4 is a side elevation of the device.

Referring first to FIG. 1, the disposable field sobriety tester 10 of this invention consists of a small, preferably plastic base plate 12 to which a relatively long, preferably cylindrical mouthpiece 14, a shorter indicator tube 16, and a balloon 18 are attached in fluid-tight relationship. The mouthpiece 14 and indicator tube 16 cooperate with the balloon 18 (through apertures 20, 22 in the base plate as best shown in FIG. 3) to form a single fluid space when the outer ends of mouthpiece 14 and indicator tube 16 are sealed as by caps 24, 26.

Preferably, the fluid space thus formed (with the balloon 18 shrunk to its minimum volume but still sealingly retained on base plate 12 by the lip 27) is filled during manufacture with an inert gas such as nitrogen just prior to the application of sealing caps 24, 26. This step dispenses with the need for desiccants in the indicator tube 16 which would otherwise be needed to keep the device dry during storage, but which would then have to be removed prior to using the tester 10. Additional shelf life protection may be achieved by enclosing the tester 10 in a sealed, nitrogen-filled transparent pouch 28 for point-of-sale display.

To use the tester 10, the sealing cap 24 is removed from the mouthpiece 14, and the balloon 18 is inflated by blowing into the mouthpiece 14. Because the mouthpiece 14 is substantially longer than the indicator tube 16, the compact juxtaposition of the tester's elements does not interfere with the use of the mouthpiece 14.

Escape of air from the balloon 18 through mouthpiece 14 is prevented by a check valve 30 consisting of a ball 32 of suitable diameter to sealingly engage a valve seat 34 formed in the mouthpiece 14. The ball 32 is preferably formed of a very lightweight material so as to be entrained by even a slight air current, and it is preferably unrestrained so as to be freely movable between the valve seat 34 and a movement-limiting clip 36 inserted into the bottom of mouthpiece 14.

When the balloon 18 has been fully inflated, the sealing cap 26 on the indicator tube 16 is removed, the air from the balloon 18 is allowed to flow through the indicator tube 16. The sealing cap 16 is affixed to the tube 16 sufficiently tightly to withstand the air pressure built up in the balloon 18 during inflation, so that it will not come off until it is deliberately removed.

The indicator tube 16 may be formed of any suitable transparent, chemically inert material and contains, in the preferred embodiment, three layers 40, 42, 44 of silica gel impregnated with dichromate in accordance with conventional techniques. Dichromate, which is normally yellow, turns green in the presence of alcohol. In the preferred embodiment, the layers 40, 42, 44 contain different concentrations of active chemicals so as to change color at alcohol concentrations of 0.5, 1.0, and 1.5 ppm, respectively, in an air stream of predetermined duration, e.g. sixty seconds. The layers 40, 42, 44 are preferably separated and encased by an inert, granular material 46 (e.g. beaded glass) which holds the layers 40, 42, 44 in place but does not chemically affect the air flowing through the tube 16. The material 46 is preferably retained within the tube 16 by an inert, porous (e.g. cloth or perforated plastic) membrane 48 at each end of tube 16.

The dimensions of tube 16 and the air flow perviousness of its contents are the principal determinants of the quantity of air passing through the indicator layers 40, 42, 44 in a given length of time. Because of the small dimensions of the device (typically less than 4×2×9 cm overall with the balloon deflated), the nitrogen content of the packaged system is so small as to be negligible in terms of the tester's accuracy of measurement.

Upon removal of the cap 26, the indicator tube 16 can be observed and the color of the layers 40, 42, 44 noted upon the expiration of, e.g., sixty seconds. The indication may then be preserved, if desired, by replacing the sealing cap 26. The tester 10 is, of course, not reusable.

The compactness and simplicity of the tester 10 allows it to be manufactured and distributed at a point-of-sale price less than that of a single cocktail, thus making it practical as a simple self-tester for persons intending to drive after consuming alcoholic beverages. The simple three-step operation of the tester 10 also facilitates its accurate use even in the hands of somewhat intoxicated persons.

We claim:

1. A disposable field sobriety tester, comprising:
   (a) a base plate;
   (b) inflatable balloon means having a single interior chamber and attached to said base plate in fluidtight relation thereto providing a fluid sample flowpath into and out of said balloon means;
   (c) mouthpiece means having two ends and being fixedly attached at one end to said base plate in fluidtight relation thereto, said base plate having formed therein a first aperture providing a fluid path between said mouthpiece means and the interior chamber via said sample flowpath of said balloon means, and said mouthpiece means having check valve means associated therewith to prevent fluid backflow from said interior chamber of said balloon means through said mouthpiece means; and
   (d) indicator means having two ends and being fixedly attached at one end to said base plate in fluidtight relation thereto, said base plate having formed therein a second aperture providing a fluid path between the interior chamber of said balloon means and said indicator means via said sample flowpath, whereby said first and second aperture communicate through said interior chamber of said balloon means; and
   (e) alcohol responsive reagent means contained within said indicator means and providing a visual indication when exposed to fluid containing alcohol vapors.

2. The tester of claim 1, in which said check valve means include a freely movable light ball member arranged to sealingly engage valve seat means formed in said mouthpiece means, and clip means lodged in said mouthpiece means, said clip means being sized and positioned so as not to obstruct fluid passage through said mouthpiece means but to limit movement of said ball member away from said valve seat means.

3. The tester of claim 1, in which said mouthpiece means are located on the same side of said base plate as said indicator means, and generally parallel and adjacent thereto, and said mouthpiece means are substantially longer than said indicator means.

4. The tester of claim 1, further comprising individually removable sealing means for sealing the ends of said mouthpiece means and indicator means remote from said base plate in fluidtight relationship, the sealing means associated with said indicator means being sufficient to withstand the fluid pressure in said balloon means when said balloon means are fully inflated.

5. The tester of claim 4, in which said mouthpiece means and indicator means are filled with an inert gas while they are sealed.

6. The tester of claim 1, in which said indicator means consist of transparent inert tube means containing at least one layer of alcohol-responsive material enclosed between layers of inert packing material.

7. The tester of claim 6, in which said indicator means consist of a plurality of layers of material responsive to different levels of alcohol vapor concentration, each of said layers being enclosed between layers of inert, non-removable packing material.

* * * * *

UNITED STATES PATENT AND TRADEMARK OFFICE
CERTIFICATE OF CORRECTION

PATENT NO. : 4,492,673
DATED : 08 JANUARY 1985
INVENTOR(S) : ERIKSEN and PAYNE

It is certified that error appears in the above—identified patent and that said Letters Patent is hereby corrected as shown below:

Column 1, line 32    "for" should read --by--;

Column 2, line 43    "the" in the second instance should read --and--;

Signed and Sealed this

Twenty-fifth Day of June 1985

[SEAL]

Attest:

DONALD J. QUIGG

Attesting Officer    Acting Commissioner of Patents and Trademarks